United States Patent

Buj et al.

Patent Number: 6,118,006
Date of Patent: Sep. 12, 2000

[54] METHOD FOR PREPARING A TETRAHYDROPYRIDIN DERIVATIVE

[75] Inventors: Michel Buj, Casteinsu le Lez; Robert Filhol, Montpellier, both of France

[73] Assignee: Sanofi-Synthelabo, Paris, France

[21] Appl. No.: 09/331,521

[22] PCT Filed: Dec. 23, 1997

[86] PCT No.: PCT/FR97/02395

§ 371 Date: Jun. 22, 1999

§ 102(e) Date: Jun. 22, 1999

[87] PCT Pub. No.: WO98/28273

PCT Pub. Date: Jul. 2, 1998

[30] Foreign Application Priority Data

Dec. 23, 1996 [FR] France ............................ 96 15906

[51] Int. Cl.[7] .................. C07D 211/72; C07D 211/84
[52] U.S. Cl. ............................................................ 546/346
[58] Field of Search ............................................ 546/346

[56] References Cited

U.S. PATENT DOCUMENTS 3,910,931 10/1975 Cavalla et al. ............................ 514/277
4,521,428  6/1985 Nisato et al. ............................. 514/277

FOREIGN PATENT DOCUMENTS 0101381  8/1983 European Pat. Off. .
0 101 381 A1  2/1984 European Pat. Off. .
1 392 194  4/1975 United Kingdom .

OTHER PUBLICATIONS

Verlag, Georg Thieme, "Method der Organischen Chemie", Band V/4, Stuttgart, pp. 679–685 (1960).

Novak, Lajos et al., "Synthesis of Novel HMG–CoA Reductase Inhibitors. I. Naphthalene anaglos of mevinolin", Liebigs Ann. Chem. (1992), (2), pp. 145–157.

Lawesson, "Anomalous reactions of 2–naphthylmethylmagnesium bromide", Acta Chemical Scandinavica, No. 12, 1958, pp. 1–7.

*Primary Examiner*—D. Margaret Seaman
*Attorney, Agent, or Firm*—Michael D. Alexander

[57] ABSTRACT

The invention relates to a method for the preparation of 1-[2-(2-naphthyl)ethyl]-4-(3-trifluoromethylphenyl)-1,2,3,6-tetrahydropyridine and its pharmaceutically acceptable salts by reacting 2-(2-bromoethyl)naphthalene with 4-(3-trifluoromethylphenyl)-1,2,3,6-tetrahydropyridine or one of its salts, and to a universal method for the preparation of the same product and its salts by the reduction of naphthylacetic acid, treatment of the resulting 2-naphthylethanol with hydrobromic acid and treatment of the 2-(2-bromoethyl) naphthalene with 4-(3-trifluoromethylphenyl)-1,2,3,6-tetrahydropyridine or one of its salts.

19 Claims, No Drawings

METHOD FOR PREPARING A TETRAHYDROPYRIDIN DERIVATIVE

The present invention relates to a method for the preparation of 1-[2-(2-naphthyl)ethyl]-4-(3-trifluoromethylphenyl)-1,2,3,6-tetrahydropyridine and its pharmaceutically acceptable salts.

1-[2-(2-Naphthyl)ethyl]-4-(3-trifluoromethylphenyl)-1,2,3,6-tetrahydropyridine, hereafter designated by its code number SR 57746, and its pharmaceutically acceptable salts were first described in EP 0 101 381 as anorexigenic agents and subsequently as antianxiodepressants (U.S. Pat. No. 5,026,716), anticonstipation agents (U.S. Pat. No. 5,109,005), neurotrophic agents (U.S. Pat. No. 5,270,320), free radical scavengers (U.S. Pat. No. 5,292,745) and cardioprotective agents (U.S. Pat. No. 5,378,709).

The document EP 0 101 381 describes a series of 1-(hetero)aralkyl-4-(3-trifluoromethylphenyl)-1,2,3,6-tetrahydropyridines prepared by condensing 4-(3-trifluoromethylphenyl)-1,2,3,6-tetrahydropyridine:

either with a (hetero)aralkyl halide, especially a chloride, bromide or iodide, or an analogous derivative containing an electrophilic leaving group such as the methanesulfonyloxy or p-toluenesulfonyloxy group;

or, if the alkylene group is linear, with a (hetero) aralkanecarboxylic acid halide, said condensation reaction being followed by reduction of the resulting amide.

According to the document cited above, 1-[2-(2-naphthyl)ethyl]-4-(3-trifluoromethylphenyl)-1,2,3,6-tetrahydropyridine is prepared in the form of the hydrochloride by reacting 4-(3-trifluoromethylphenyl)-1,2,3,6-tetrahydropyridine with 2-naphthylacetyl chloride and reducing the resulting product with lithium aluminum hydride. This method proceeds satisfactorily in the first step, but the subsequent reduction causes a loss of yield due to attack of the trifluoromethyl group by the reducing agent, as demonstrated by the yield of 42.73% of theory obtained in the preparation described.

The same document describes the preparation of 1-[2-(2-naphthyl)ethyl]-4-(3-trifluoromethylphenyl)-1,2,3,6-tetrahydropyridine hydrochloride by condensing 4-(3-trifluoromethylphenyl)-1,2,3,6-tetrahydropyridine with 2-(2-chloroethyl)naphthalene in the presence of triethylamine, but gives no indication of the yields obtained. Independently of the yields which can be obtained by this alkylation, however, the use of 2-(2-chloroethyl) naphthalene gives rise to problems associated with the manufacture of this intermediate, which involves heating 2-(2-naphthyl)ethanol in thionyl chloride. This reaction gives very low yields of chlorinated derivative, on the one hand because the naphthylethanol does not react completely and on the other hand because the reaction gives variable amounts—according to the operating conditions—of 2-vinylnaphthalene.

Better yields (83.9%) are obtained by reacting 2-naphthalenethanol with thionyl chloride in ether in the presence of pyridine (J. Am. Chem. Soc., 1982, 104 (19): 5171), but this type of reaction has to be followed with very great care and, in particular, is difficult to exploit on the industrial scale.

It has also been found that the reaction of 2-(2-chloroethyl)naphthalene with 4-(3-trifluoromethylphenyl)-1,2,3,6-tetrahydropyridine under the conditions described in EP 0 101 381, i.e. in ethanol under reflux for 20–24 hours, gives 1-[2-(2-naphthyl)ethyl]-4-(3-trifluoromethylphenyl)-1,2,3,6-tetrahydropyridine hydrochloride with very low yields.

It has now been found that by reacting 4-(3-trifluoromethylphenyl)-1,2,3,6-tetrahydropyridine or one of its salts with 2-(2-bromoethyl)naphthalene, 1-[2-(2-naphthyl)ethyl]-4-(3-trifluoromethylphenyl)-1,2,3,6-tetrahydropyridine and its salts can be obtained with yields well above those obtained according to EP 0 101 381.

It has also been found that the products obtained in this way are purer than the 1-[2-(2-naphthyl)ethyl]-4-(3-trifluoromethylphenyl)-1,2,3,6-tetrahydropyridine hydrochloride prepared using 2-(2-chloroethyl)naphthalene according to EP 0 101 381, because they are practically devoid of vinyl derivatives. Furthermore, the 2-(2-bromoethyl)naphthalene used as reactant can be prepared very easily, with yields in excess of 90%, from 2-naphthylethanol and hydrobromic acid, and the product obtained contains 2-vinylnaphthalene in amounts of not more than 0.1%, or none at all.

Finally, it has been found that 2-(2-bromoethyl) naphthalene can be obtained directly from naphthylacetic acid without isolating the 2-naphthylethanol with excellent yields, even in excess of 80%.

Thus, according to one of its aspects, the present invention relates to a method for the preparation of 1-[2-(2-naphthyl)ethyl]-4-(3-trifluoromethylphenyl)-1,2,3,6-tetrahydropyridine of formula (1):

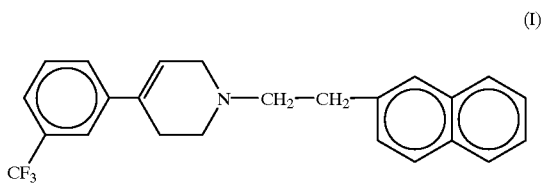

(I)

and its pharmaceutically acceptable salts, characterized in that 4-(3-trifluoromethylphenyl)-1,2,3,6-tetrahydropyridine of formula (II):

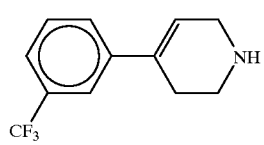

(II)

or one of its salts, is treated with 2-(2-bromoethyl) naphthalene of formula (III):

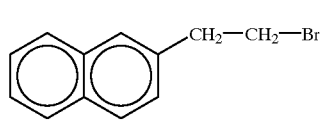

(III)

in the presence of a base and at a temperature between 20° C. and the reflux temperature of the solvent employed.

It is immaterial whether the 4-(3-trifluoromethylphenyl)-1,2,3,6-tetrahydropyridine of formula (II) used as the starting compound of formula (II) is in the form of the free base or one of its salts, the hydrochloride being preferred in the latter case.

The solvent can be protic or aprotic and is preferably polar, for example a $C_1$–$C_3$ alcohol such as methanol or ethanol, either by itself or mixed with water, acetonitrile or a ketone such as acetone or methyl isobutyl ketone.

In one advantageous procedure, the reaction is carried out using the compound of formula (II) in the form of the hydrochloride. More advantageously, 4-(3-trifluoromethylphenyl)-1,2,3,6-tetrahydropyridine hydrochloride is reacted with 2-(2-bromoethyl)naphthalene in a polar protic or aprotic solvent, such as those mentioned above, under reflux and in the presence of a base.

In one particularly advantageous procedure, the reaction of the compound (II) in the form of the hydrochloride with the compound (II) is carried out in a solvent selected from ethanol/water mixtures, acetonitrile and acetone, at the reflux temperature, in the presence of a base selected from alkali metal hydroxides and carbonates.

Under these particularly advantageous conditions, the reaction is complete after 3–8 hours of heating and the compound of formula (I) is isolated by the conventional techniques, for example either by simple filtration of the free base thereby obtained, or by treatment with a solution of an acid to recover the corresponding salt; this can then be neutralized to give the free base, which in turn can be converted to one of its pharmaceutically acceptable salts. The yields of final product under these conditions are very satisfactory and can reach 80–90%.

The compound of formula (I) obtained by this method has a very high purity and, in particular, does not contain a detectable amount of vinyl derivative, in contrast to a product obtained from chloroethylnaphthalene according to EP 0 101 381.

As mentioned above, the use of 2-(2-chloroethyl)naphthalene has the disadvantage that the preparation of the product by reacting 2-(2-naphthyl)ethanol with thionyl chloride also gives very low yields because of the formation of appreciable amounts of 2-vinylnaphthalene, which are removed during the isolation of the desired product.

These secondary reactions do not take place according to another aspect of the present invention, which consists in preparing 2-(2-bromoethyl)naphthalene by a method characterized in that 2-naphthylacetic acid is reduced and the resulting crude 2-(2-naphthyl)ethanol is then treated with concentrated hydrobromic acid.

The reduction is preferably effected with an optionally mixed hydride of boron or aluminum selected from lithium aluminum hydride, sodium bis(2-methoxyethoxy)aluminum hydride and diborane, in an ether-type organic solvent such as methyl t-butyl ether, dioxane or tetrahydrofuran.

In one preferred procedure, naphthylacetic acid is treated with lithium aluminum hydride in tetrahydrofuran, advantageously at a temperature below 20° C., and, after removal of the salts, for example by the addition of an alkali metal hydroxide and removal of the insoluble material by filtration, the tetrahydrofuran is evaporated off and the residue, consisting of crude 2-(2-naphthyl)ethanol, is treated with concentrated hydrobromic acid (47–48%). 2-(2-Bromoethyl)naphthalene is thus isolated with very high yields, even in excess of 80%, relative to the starting naphthylacetic acid.

Furthermore, the 2-(2-bromoethyl)naphthalene obtained by this procedure is very pure, because it contains less than 0.1% of vinyl derivative.

According to a preferred aspect, the present invention relates especially to a method for the preparation of 1-[2-(2-naphthyl)ethyl]-4-(3-trifluoromethylphenyl)-1,2,3,6-tetrahydropyridine and its pharmaceutically acceptable salts, characterized in that:

(a) 2-naphthylacetic acid is reduced to 2-(2-naphthyl)ethanol and the resulting product, without purifying it, is reacted with concentrated hydrobromic acid;

(b) then the resulting 2-(2-bromoethyl)naphthalene is treated with 4-(3-trifluoromethylphenyl)-1,2,3,6-tetrahydropyridine or one of its salts in the presence of a base; and (c) the 1-[2-(2-naphthyl)ethyl]-4-(3-trifluoromethylphenyl)-1,2,3,6-tetrahydropyridine is isolated either in the form of the base, which is optionally converted to one of its pharmaceutically acceptable salts, or in the form of one of its salts, which is optionally neutralized to give the free base.

Step (a) is preferably carried out using an optionally mixed hydride of boron or aluminum as the reducing agent, lithium aluminum hydride, sodium bis(2-methoxyethoxy) aluminum hydride and diborane being particularly advantageous.

Diborane is normally used in the form of one of its complexes, for example with dimethyl sulfide or tetrahydrofuran. This complex can easily be generated in situ.

Lithium aluminum hydride is the preferred reducing agent.

The reduction is preferably effected in tetrahydrofuran, at a temperature below 20° C. if the reducing agent is lithium aluminum hydride, or under reflux if the reducing agent used is diborane.

When the reduction has ended, the reducing agent is destroyed by the conventional methods, for example with a base such as sodium hydroxide, the salts are removed with the aqueous phase and, after evaporation of the solvent, the resulting crude 2-(2-naphthyl)ethanol is reacted directly with concentrated hydrobromic acid. This bromination is effected under reflux and is complete after 4–8 hours of heating.

The 2-(2-bromoethyl)naphthalene which is thus obtained with a yield in excess of 80%, relative to the naphthylacetic acid, is isolated by simple filtration and crystallized from isopropanol. It is pure and does not contain a detectable amount of vinyl derivative.

Step (b), namely the reaction of the resulting 2-(2-bromoethyl)naphthalene with 4-(3-trifluoromethylphenyl)-1,2,3,6-tetrahydropyridine or, preferably, its hydrochloride is advantageously carried out in a polar protic or aprotic solvent. Preferably, it takes place with very good yields, and without the formation of vinyl derivatives, in a solvent selected from acetonitrile, acetone and water/ethanol mixtures under reflux, in the presence of a base selected from alkali metal hydroxides and carbonates.

In one particularly advantageous procedure, 2-(2-bromoethyl)naphthalene is treated with 4-(3-trifluoromethylphenyl)-1,2,3,6-tetrahydropyridine hydrochloride in a 2/1 to 1/1 (v/v) water/ethanol mixture, in the presence of an alkali metal hydroxide, especially sodium hydroxide, under reflux, and the reaction is generally complete after 4–6 hours.

In step (c), 1-[2-(2-naphthyl)ethyl]-4-(3-trifluoromethylphenyl)-1,2,3,6-tetrahydropyridine, obtained in step (b) with a yield which can reach 90% of theory under the conditions of the particularly advantageous procedure illustrated above, is isolated either in the form of the free base or in the form of one of its salts.

In the particularly advantageous procedure illustrated above, the use of the aqueous-alcoholic solvent makes it possible, when the reaction mixture cools, to precipitate 1-[2-(2-naphthyl)ethyl]-4-(3-trifluoromethylphenyl)-1,2,3,6-tetrahydropyridine base, which can be isolated by simple filtration, washed with water and dried.

The resulting free base can be converted to one of its pharmaceutically acceptable salts by treatment with a solution of the appropriate acid in an organic or aqueous-organic solvent, and crystallization.

The preferred pharmaceutically acceptable salt, the hydrochloride, can be obtained by reaction of the base with a solution of hydrochloric acid in ethanol and crystallization from an appropriate solvent such as ethanol, an ethanol/water mixture, acetone, methyl ethyl ketone, ethyl acetate or a mixture of these with water, an ethanol/hydrochloric acid mixture or dimethyl sulfoxide.

The 1-[2-(2-naphthyl)ethyl]-4-(3-trifluoromethylphenyl)-1,2,3,6-tetrahydropyridine can also be isolated in the form of one of its pharmaceutically acceptable or unacceptable salts, from which the free base can be liberated by neutralization, for example with an alkali metal hydroxide, and optionally converted to a pharmaceutically acceptable salt as illustrated above. The 1-[2-(2-naphthyl)ethyl]-4-(3-trifluoromethylphenyl)-1,2,3,6-tetrahydropyridine is preferably isolated in the form of its preferred salt, the hydrochloride, which is recrystallized from appropriate solvents such as those mentioned above.

The following Examples illustrate the invention.

EXAMPLE 1

A mixture of 12.5 g of 2-(2-bromoethyl)naphthalene, 14 g of 4-(3-trifluoromethylphenyl)-1,2,3,6-tetrahydropyridine hydrochloride, 4.34 g of sodium hydroxide, 135 ml of water and 95 ml of 95% ethanol is refluxed for 5 hours, the reaction mixture is subsequently allowed to cool to room temperature overnight and then filtered and the product isolated in this way is washed with water and dried under vacuum at 50° C. to give 1-[2-(2-naphthyl)ethyl]-4-(3-trifluoromethylphenyl)-1,2,3,6-tetrahydropyridine base with a yield of 90%, calculated relative to the starting 4-(3-trifluoromethylphenyl)-1,2,3,6-tetrahydropyridine hydrochloride.

EXAMPLE 2

A mixture of 6.25 g of 2-(2-bromoethyl)naphthalene, 7 g of 4-(3-trifluoromethylphenyl)-1,2,3,6-tetrahydropyridine hydrochloride, 3.75 g of potassium carbonate and 100 ml of acetone is refluxed for 4 hours and the reaction mixture is then allowed to cool to room temperature. The salts formed are filtered off and discarded. The solvent is evaporated off and the residue is taken up with a solution of hydrochloric acid in ethanol to give 1-[2-(2-naphthyl)ethyl]-4-(3-trifluoromethylphenyl)-1,2,3,6-tetrahydropyridine hydrochloride, which is recrystallized from ethanol. Yield: 70% of theory, relative to the starting 4-(3-trifluoromethylphenyl)-1,2,3,6-tetrahydropyridine hydrochloride. The product obtained is in the form of a fine white crystalline powder having an HPLC purity of 99.9%.

EXAMPLE 3

By using the operating conditions described in Example 2 and refluxing for three hours in acetonitrile, 1-[2-(2-naphthyl)ethyl]-4-(3-trifluoromethylphenyl)-1,2,3,6-tetrahydropyridine hydrochloride having an HPLC purity of 99.9% is isolated with a yield of 80.1%, calculated relative to the starting 4-(3-trifluoromethylphenyl)-1,2,3,6-tetrahydropyridine hydrochloride.

EXAMPLE 4

6.25 ml of concentrated hydrochloric acid are added, with stirring, to a solution of 17.2 g of 1-[2-(2-naphthyl)ethyl]-4-(3-trifluoromethylphenyl)-1,2,3,6-tetrahydropyridine base, obtained according to Example 1, in 200 ml of absolute ethanol. The resulting mixture is refluxed for 90 minutes, after which the solution is first filtered hot and then evaporated to remove about 100 ml of solvent. 20 ml of distilled water are added to the mixture, the temperature of the solution is brought to 75° C. and said solution is then cooled to 5° C. at a rate of 10° C. per hour. The mixture is kept at 5° C. for about one hour and the product is then collected by filtration and washed with a mixture of 32 ml of absolute ethanol and 3 ml of water. The product is dried under vacuum at 50° C. to give 1-[2-(2-naphthyl)ethyl]-4-(3-trifluoromethylphenyl)-1,2,3,6-tetrahydropyridine hydrochloride.

EXAMPLE 5 a/ 2-(2-Bromoethyl)naphthalene

A solution of 27.8 kg of 2-naphthylacetic acid in 95 l of tetrahydrofuran is added, at a temperature below 20° C., to a mixture of 27.5 l of tetrahydrofuran and 10 kg of lithium aluminum hydride. The mixture is cooled to 0° C. and the following are then added slowly: firstly 10 l of water, then a solution of 1.5 kg of sodium hydroxide in 10 l of water, and finally 30 l of water. The salts which separate out are washed with 160 l of tetrahydrofuran and then filtered off. The combined tetrahydrofuran solutions are evaporated and the residue, consisting of an estimated 24.5 kg of 2-(2-naphthyl)ethanol, is treated with 138 l of concentrated hydrobromic acid. The mixture is refluxed for 5 hours and allowed to return to room temperature, with stirring, and the product obtained is then filtered off and washed with water. The moist product is dissolved in 147 l of isopropanol under reflux, about 75 l of solvent are removed by distillation and the mixture is allowed to cool overnight. The product which has crystallized in this way is filtered off, washed with previously cooled isopropanol and dried under vacuum at 40° C. The 2-(2-bromoethyl)naphthalene obtained does not contain a detectable amount of vinyl derivative. Yield: 81%, calculated relative to the starting naphthylacetic acid.

b/ 1-[2-(2-Naphthyl)ethyl]-4-(3-trifluoromethylphenyl)-1,2,3,6-tetrahydropyridine 12.5 kg of 2-(2-bromoethyl)naphthalene and 14 kg of 4-(3-trifluoromethylphenyl)-1,2,3,6-tetrahydropyridine hydrochloride are added to a mixture of 4.34 kg of sodium hydroxide, 135 l of water and 95 l of 95% ethanol. The reaction mixture is refluxed for at least 4 hours and is then left to cool to room temperature overnight so as to allow the reaction product to precipitate out.

c/ Isolation of the Base

The precipitate obtained in operation (b) is collected by filtration and washed twice with 14 l portions of water; the product is then dried under vacuum at about 50° C. This gives 1-[2-(2-naphthyl)ethyl]-4-(3-trifluoromethylphenyl)-1,2,3,6-tetrahydropyridine base. M.p. 129–131° C. Overall yield, calculated relative to the starting 2-naphthylacetic acid: 74.3%.

EXAMPLE 6

In two different preparations, 4-(3-trifluoromethylphenyl)-1,2,3,6-tetrahydropyridine is reacted, in the presence of triethylamine, with 2-(2-bromoethyl)naphthalene (PREPARATION A) and respectively with 2-(2-chloroethyl)naphthalene (PREPARATION B) in ethanol under reflux for 20 hours. The reaction mixtures of the two preparations were concentrated, the residue was taken up with ethyl ether and the ether solution, which was filtered and washed with water, was dried and evaporated. The residue was taken up with a solution of gaseous hydrochloric acid in isopropanol to give 1-[2-(2-naphthyl)ethyl]-4-(3-trifluoromethylphenyl)-1,2,3,6-tetrahydropyridine hydrochloride, which was crystallized from ethanol.

PREPARATION A: Yield: 59.8% HPLC purity: 99.9% Estimated vinyl content: not detectable
PREPARATION B: Yield: 7.5% HPLC purity: 97.8% Estimated vinyl content: 2.1%

What is claimed is:

1. A method for the preparation of 1-[2-(2-naphthyl)ethyl]-4-(3-trifluoromethylphenyl)-1,2,3,6-tetrahydropyridine of formula (I):

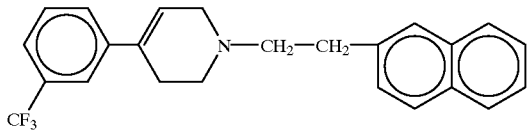

(I)

and its pharmaceutically acceptable salts, wherein 4-(3-trifluoromethylphenyl)-1,2,3,6-tetrahydropyridine of formula (II):

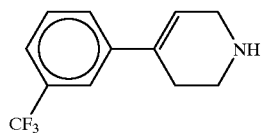

(II)

or one of its salts, is treated with 2-(2-bromoethyl)naphthalene of formula (III):

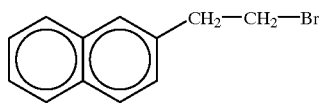

(III)

in the presence of a base and at a temperature between 20° C. and the reflux temperature of the solvent employed.

2. A method according to claim 1 wherein the compound (II) is used in the form of the hydrochloride.

3. A method according to claim 2 wherein the reaction is carried out in a polar protic or aprotic solvent under reflux.

4. A method according to claim 3 wherein the reaction is carried out in a solvent selected from acetone, acetonitrile and water/ethanol mixtures, in the presence of a base selected from alkali metal hydroxides and carbonates.

5. A method for the preparation of 2-(2-bromoethyl)naphthalene, wherein 2-naphthylacetic acid is reduced and then the resulting crude 2-(2-naphthyl)ethanol is treated with concentrated hydrobromic acid.

6. A method according to claim 5 wherein the reduction is effected with an optionally mixed hydride of boron or aluminum selected from lithium aluminum hydride and diborane.

7. A method according to claim 5, wherein the 2-naphthylacetic acid is reduced with lithium aluminum hydride in tetrahydrofuran and, after removal of the salts and evaporation of the solvent, the residue is treated with concentrated hydrobromic acid.

8. A method for the preparation of 1-[2-(2-naphthyl)ethyl]-4-(3-trifluoromethylphenyl)-1,2,3,6-tetrahydropyridine and its pharmaceutically acceptable salts wherein:

(a) 2-naphthylacetic acid is reduced to 2-(2-naphthyl)ethanol and the resulting product, without purifying it, is reacted with concentrated hydrobromic acid;

(b) then the resulting 2-(2-bromoethyl)naphthalene is treated with 4-(3-trifluoromethylphenyl)-1,2,3,6-tetrahydropyridine or one of its salts; and (c) the 1-[2-(2-naphthyl)ethyl]-4-(3-trifluoromethylphenyl)-1,2,3,6-tetrahydropyridine is isolated either in the form of the base, which is optionally converted to one of its pharmaceutically acceptable salts, or in the form of one of its salts, which is optionally neutralized to give the free base.

9. A method according to claim 8 wherein lithium aluminum hydride is used as the reducing agent in step (a).

10. A method according to claim 9 wherein the reduction is effected in tetrahydrofuran.

11. A method according to claim 8 wherein 4-(3-trifluoromethylphenyl)-1,2,3,6-tetrahydropyridine hydrochloride is used in step (b).

12. A method according to claim 11 wherein the reaction of step (b) is carried out in a polar protic or aprotic solvent in the presence of a base.

13. A method according to claim 12 wherein the polar protic or aprotic solvent is selected from acetonitrile, acetone and ethanol/water mixtures under reflux, and the base is selected from alkali metal hydroxides and carbonates.

14. A method according to claim 13 wherein step (b) is carried out by treating 2-(2-bromoethyl)naphthalene in a 2/1 to 1/1 (v/v) ethanol/water mixture, in the presence of an alkali metal hydroxide, under reflux.

15. A method according to claim 14 wherein sodium hydroxide is used as the alkali metal hydroxide.

16. A method according to claim 14 wherein in step (c), 1-[2-(2-naphthyl)ethyl]-4-(3-trifluoromethylphenyl)-1,2,3,6-tetrahydropyridine base is isolated by filtration and optionally converted to one of its pharmaceutically acceptable salts.

17. A method according to claim 16 wherein the base obtained is converted to its hydrochloride.

18. A method according to claim 15 wherein in step (c), 1-[2-(2-naphthyl)ethyl]-4-(3-trifluoromethylphenyl)-1,2,3,6-tetrahydropyridine base is isolated by filtration and optionally converted to one of its pharmaceutically acceptable salts.

19. A method according to claim 18 wherein the base obtained is converted into its hydrochloride.

* * * * *